United States Patent
Abbott et al.

(10) Patent No.: US 11,464,397 B2
(45) Date of Patent: Oct. 11, 2022

(54) SOFT ROBOT TO NAVIGATE THE NATURAL LUMENS OF A LIVING ORGANISM USING UNDULATORY LOCOMOTION GENERATED BY A ROTATING MAGNETIC DIPOLE FIELD

(71) Applicant: University of Utah Research Foundation, Salt Lake City, UT (US)

(72) Inventors: Jacob J Abbott, Salt Lake City, UT (US); Lan N. Pham, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 364 days.

(21) Appl. No.: 16/586,856

(22) Filed: Sep. 27, 2019

(65) Prior Publication Data

US 2020/0100658 A1 Apr. 2, 2020

Related U.S. Application Data

(60) Provisional application No. 62/737,716, filed on Sep. 27, 2018.

(51) Int. Cl.
*A61B 1/00* (2006.01)
*B63H 21/17* (2006.01)
*A61B 1/005* (2006.01)

(52) U.S. Cl.
CPC ........ *A61B 1/00156* (2013.01); *A61B 1/0016* (2013.01); *A61B 1/0051* (2013.01); *A61B 1/00158* (2013.01); *B63H 21/17* (2013.01)

(58) Field of Classification Search
CPC . A61B 1/00156; A61B 1/00158; A61B 1/041; A61B 1/0016
See application file for complete search history.

(56) References Cited

U.S. PATENT DOCUMENTS 7,708,687 B2   5/2010   Bern et al.
8,444,550 B2   5/2013   Kawano et al.
(Continued)

FOREIGN PATENT DOCUMENTS

CN   106114668   11/2016
CN   106344018   1/2017
(Continued)

OTHER PUBLICATIONS azorobotics.com.; "Researchers Successfully Manipulate Soft Robots Using Magnetic Fields." Taken from: https://www.azorobotics.com/News.aspx?newsID=9050; Mar. 30, 2017, 3 Pages.
(Continued)

*Primary Examiner* — Aaron B Fairchild
(74) *Attorney, Agent, or Firm* — Thorpe North and Western LLP

(57) ABSTRACT

A system for propelling a magnetic robotic device through a human comprises a magnetic actuator device operable to generate a rotating magnetic field, and a magnetic robotic device comprising a compliant body and at least two permanent magnets supported by and spatially separated about the compliant body. A non-magnetic region can also be oriented between the at least two permanent magnets. The at least two permanent magnets can be alternating or non-alternating in polarity with each other. In response to application of the rotating magnetic field generated by the magnetic actuator device and that is situated proximate the magnetic robotic device, the rotating magnetic field effectuates undulatory locomotion of the magnetic robotic device to propel the magnetic robotic device through a human, such as through a natural lumen. Further, the magnetic robotic device can optionally be supported by a catheter or endoscope to assist with propelling a distal end through a human.

20 Claims, 16 Drawing Sheets

(56) References Cited

U.S. PATENT DOCUMENTS

| | | |
|---|---|---|
| 8,803,643 B2 | 8/2014 | Mahoney et al. |
| 9,308,387 B2 | 4/2016 | Phillips et al. |
| 2012/0035437 A1 | 2/2012 | Ferren et al. |
| 2012/0303965 A1 | 11/2012 | Carter et al. |
| 2013/0303847 A1* | 11/2013 | Sitti .................. A61B 1/041 600/101 |
| 2018/0116744 A1 | 5/2018 | Taya |
| 2018/0326578 A1 | 11/2018 | Kwok et al. |
| 2020/0035390 A1* | 1/2020 | Hu ..................... H01F 1/0308 |

FOREIGN PATENT DOCUMENTS

| | | |
|---|---|---|
| KR | 101488247 | 2/2015 |
| WO | WO 2013/110086 A1 | 7/2013 |
| WO | WO 2018/130410 A1 | 7/2018 |

OTHER PUBLICATIONS

Mahoney et al.; "Velocity Control with Gravity compensation for Magnetic Helical Microswimmers." Advanced Robotics; 2011; vol. 25; pp. 1007-1028.

Petruska et al.; "First Demonstration of a Modular and Reconfigurable Magnetic-Manipulation System." In Proc. IEEE Int. Conf. Robotics and Automation; May 26-30, 2015; Seattle, Washington; pp. 149-155.

* cited by examiner

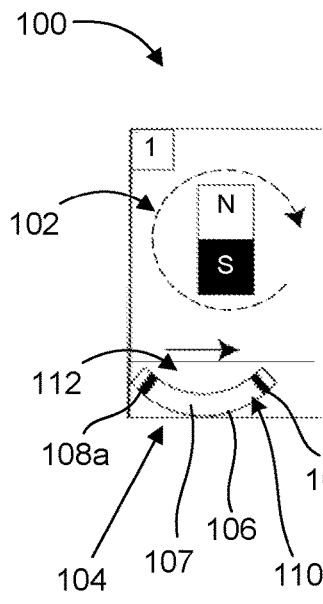
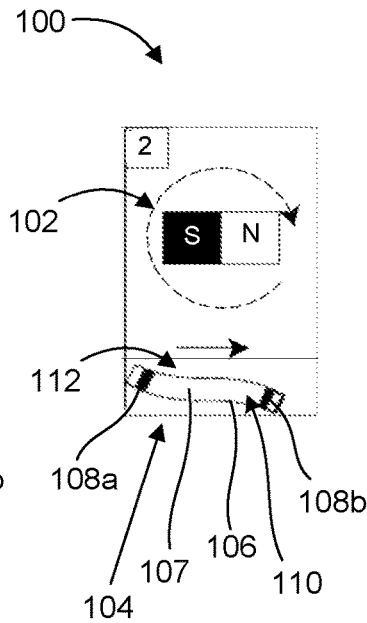
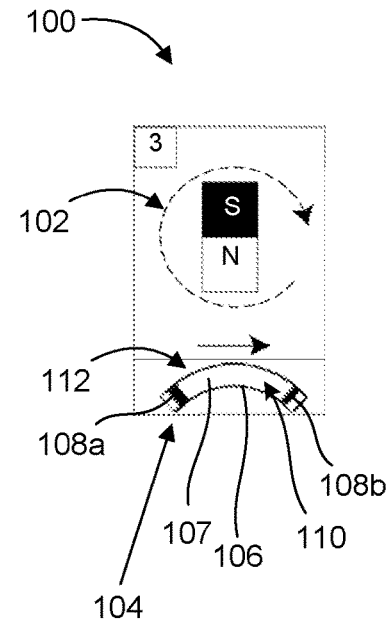
FIG. 1a        FIG. 1b        FIG. 1c
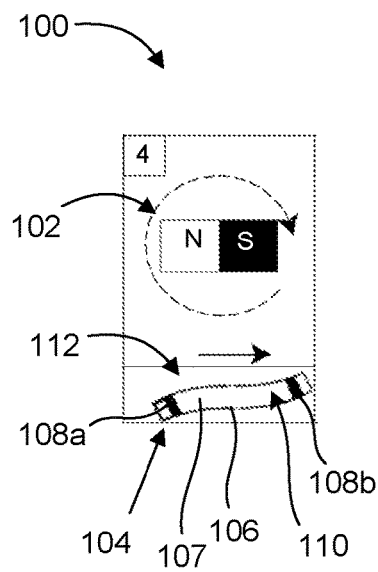
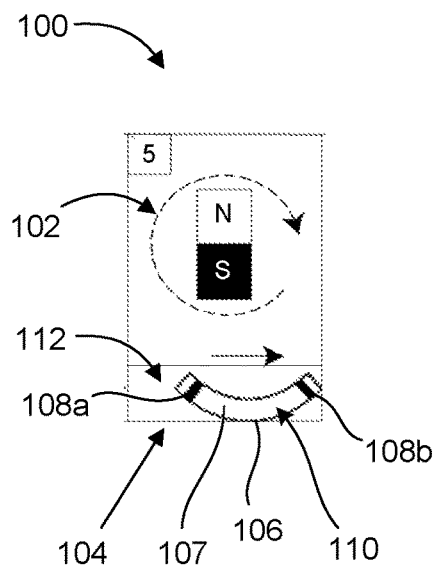
FIG. 1d        FIG. 1e

SOFT ROBOT TO NAVIGATE THE NATURAL LUMENS OF A LIVING ORGANISM USING UNDULATORY LOCOMOTION GENERATED BY A ROTATING MAGNETIC DIPOLE FIELD

RELATED APPLICATION

This application claims the benefit of U.S. Provisional Patent Application Ser. No. 62/737,716, filed Sep. 27, 2018, which is herein incorporated by reference in its entirety.

GOVERNMENT INTEREST

None.

BACKGROUND

Magnetic microscale and mesoscale devices, such as capsule endoscopes and microrobots, can be manipulated with an externally generated magnetic field. The magnetic field applies a combination of force and torque to the device without a mechanical connection. Magnetic manipulation systems have been used to drag a device along a path, roll a device across a surface, or point a device in a desired direction, such as magnetic catheters and magnetotactic bacteria.

Magnetic manipulation systems have incorporated permanent magnets and electromagnets. Although the dipole moment magnitude of a typical electromagnet can vary through a change in electrical current, the dipole moment orientation of such an electromagnet can be cumbersome to move dynamically. On the other hand, the dipole moment orientation of a permanent magnet is typically easier to move dynamically, but its dipole moment magnitude is fixed.

A combination of permanent magnets and electromagnets can be used to produce a suitable magnetic field for a manipulation task. Some tasks, however, tend to be better suited to either permanent magnet or electromagnet systems. For example, because electromagnet systems have more direct control of field strength, they have been used for multi-degree-of-freedom levitation and positioning control. Permanent magnets, which require no electrical power to generate a field, are well-suited for pulling or rolling tasks that require the magnetic source to move along complex trajectories.

A number of groups have developed bioinspired actuation technologies to enable robotic locomotion through lumens, some utilizing applied magnetic fields. Some have developed magnetic-actuation concepts that utilize a uniform rotating field and a uniform oscillating field, respectively, to generate snake-like propulsion. Both concepts comprise a series of articulated magnetic segments with protruding legs to cause asymmetric friction with lumen walls when driven by the applied magnetic field. In both of the prototypes developed, the entire device is dedicated to accomplishing the novel locomotion scheme, and it is not clear how the concepts could be incorporated into a more traditional medical device. Due to the complexity of the respective designs, neither are inherently scalable.

Others have created a flat sheet of magnetic material which is rolled up before magnetization, without requiring articulated segments. They demonstrated multiple gaits with a millimeter-scale prototype using uniform rotating magnetic fields.

Another related concept includes a miniature robot that crawls across a surface using a looping inchworm gait (i.e., reminiscent of an "inchworm" moth larva). This type of motion involves two feet, each taking turns anchoring to the ground as its body contracts and propels itself forward. Such concept again uses a uniform rotating magnetic field for actuation, with the miniature device comprising two magnetic bodies separated by a compliant structure. The device also comprises a number of additional mechanical elements that are required to transduce the magnetic field into locomotion and stop the permanent-magnet elements from sticking together. A related nonmagnetic device capable of inchworm locomotion was developed that utilizes shape-memory-alloy fibers embedded longitudinally within a soft body for actuation.

Other methods to locomote robots through tubes have been inspired by earthworm locomotion, utilizing rectilinear (i.e., straight line) motion. This type of actuation works by segments in the device sequentially widening and narrowing to change the friction properties of the respective segments with respect to the lumen wall. A similar rectilinear motion can be created even when the segments are not able to individually widen and narrow, simply by capitalizing on the friction imbalance when only one segment is moving relative to multiple stationary segments. In these rectilinear locomotion concepts, all of the motion is generated internally or come from a tether, unlike methods that utilize applied magnetic fields. As a result, the actuators within the robot have increased complexity relative to the magnetic concepts, making them more challenging to scale down to the size that would be desirable for many medical applications.

Magnetic manipulation of capsule endoscopes has the potential to make current gastrointestinal screening procedures faster, safer, and less invasive. To date, three electromagnetic systems have been developed with the ability to perform five degree-of-freedom (5-DOF) manipulation of an untethered magnetic device, such as a magnetic capsule endoscope. The MAGNETECS and OCTOMAG systems consist of eight electromagnets arranged around a sphere and hemisphere, respectively, and directed toward the manipulation workspace. A system has been developed by Siemens, consisting of twelve electromagnets through which a patient is positioned, for the control of a capsule endoscope in a water-filled stomach. Permanent-magnet actuation systems are gaining attention for their ability to generate fields with clinically relevant strengths, inexpensively and in a compact form-factor, compared to electromagnetic systems. However, such capsules are generally too large to traverse through natural lumens of a human body, such as through veins, arteries, intestines, etc.

SUMMARY

In one example, the present disclosure sets forth a magnetic robotic device comprising: a compliant body; a first permanent magnet attached to the compliant body; and a second permanent magnet attached to the compliant body and spatially separated from the first pair of permanent magnets about the compliant body. In some examples, a non-magnetic region can be located between the at least two permanent magnets. In response to application of a rotating magnetic field generated by an electromagnetic actuator device, the magnetic robotic device is operable to be propelled, via undulatory locomotion of the magnetic robotic device, through a human.

In one example, the present disclosure sets forth a system for propelling a magnetic robotic device through a human, comprising an electromagnetic actuator device operable to generate a rotating magnetic field, and a magnetic robotic device comprising a compliant body and at least two permanent magnets supported by the compliant body, such that the at least two permanent magnets are spatially separated from each other. In some examples, a non-magnetic region can be located between the at least two permanent magnets. In response to application of the rotating magnetic field by the electromagnetic actuator device situated proximate the magnetic robotic device, the rotating magnetic field effectuates undulatory locomotion of the magnetic robotic device to propel the magnetic robotic device through a human.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

BRIEF DESCRIPTION OF THE DRAWINGS

FIGS. 1a-1e are a 5-sequence graphic illustrating undulatory locomotion of a magnetic robotic device through a lumen, and as effectuated by a rotating magnetic actuator device, in accordance with an example of the present disclosure.

Figure 2A:
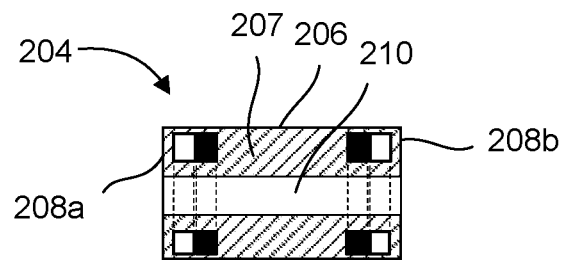
FIG. 2a illustrates a cross sectional view of a magnetic robotic device, in accordance with an example of the present disclosure.

These drawings are provided to illustrate various aspects of the invention and are not intended to be limiting of the scope in terms of dimensions, materials, configurations, arrangements or proportions unless otherwise limited by the claims.

DETAILED DESCRIPTION

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

Definitions

In describing and claiming the present invention, the following terminology will be used.

The singular forms "a," "an," and "the" include plural referents unless the context clearly dictates otherwise. Thus, for example, reference to "a lumen" includes reference to one or more of such materials and reference to "aligning" refers to one or more such steps.

As used herein, the term "about" is used to provide flexibility and imprecision associated with a given term, metric or value. The degree of flexibility for a particular variable can be readily determined by one skilled in the art. However, unless otherwise enunciated, the term "about" generally connotes flexibility of less than 2%, and most often less than 1%, and in some cases less than 0.01%.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, the term "at least one of" is intended to be synonymous with "one or more of." For example, "at least one of A, B and C" explicitly includes only A, only B, only C, and combinations of each.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

A Soft Robot to Navigate the Natural Lumens of a Living Organism Using Undulatory Locomotion Generated by a Rotating Magnetic Dipole Field A soft-robotic actuator or actuation system is provided to enable a mesoscale medical robot to navigate the natural lumens of the body, such as blood vessels and intestines. The term "soft robot" can mean a robotic device having some component or element of compliance or flexibility, such as a compliant body that can flex or bend (see below and FIGS. 1a-2d). As an overview, the system comprises a soft robot with at least two embedded permanent magnets with alternating magnetic polarity from one another, and a rotating (non-uniform) dipole magnetic field that is swept over the robot, resulting in a traveling wave undulatory motion that propels the robot forward and backward (see e.g., FIG. 1a-1e, steps 1 through 5). This "soft actuation" technology can be fabricated in a wide range of sizes, and can be applied in a variety of diagnostic and therapeutic contexts. There are a variety of benefits of using non-uniform dipole fields over using uniform fields, as well as the benefits of alternating the polarity of the magnets embedded in the device.

In one example a soft robotics actuation or actuator is provided to enable a mesoscale medical robot to navigate the natural lumens of the body, such as blood vessels and intestines. The basic method comprises a robot that has a soft body support structure with at least two embedded permanent magnets (e.g., at the two ends of the structure) with alternating magnetic polarity, and a rotating non-uniform magnetic field that is swept over the robot, resulting in an undulatory motion (i.e., traveling wave) that propels the robot forward FIGS. 1a-1e). Alternatively, the permanent magnets can be attached to an external surface of the body of the magnetic robot. For example, the permanent magnets may have an adhesive bonding the permanent magnets to the external surface. Thus, in one example shown in FIGS. 1a-1e, a system 100 for propelling a magnetic robotic device 104, such as through a natural lumen 112 of a human, can comprise an magnetic actuator device 102 operable to generate a rotating magnetic field to effectuate undulatory locomotion of the magnetic robotic device 104, as further detailed herein. The magnetic actuator device 102 can be one or more permanent magnets which are movable relative to the magnetic robotic device 104. Alternatively, the magnetic actuator device 102 can be an electromagnetic actuator having a manipulable magnetic dipole strength and direction. Typically, the magnetic actuator device 102 can be oriented adjacent and external to the lumen in which the magnetic robotic device 102 is positioned. Thus, in some cases the magnetic actuator device 102 can be in direct contact with an exterior surface of a patient, or there can be a gap between the exterior surface and the actuator as long as a sufficiently strong magnetic field can be generated at the magnetic robotic device 104 to effectuate the desired undulatory locomotion. Thus, a non-uniform magnetic field is one that applies varying magnetic dipole direction to the magnetic robotic device, and in some cases also applies a varied magnetic field strength.

The magnetic robotic device 104 can comprise a flexible or compliant body 106, a first permanent magnet 108a attached to the compliant body 106, and a second permanent magnet 108b attached to the compliant body and spatially separated from the first permanent magnets 108a about the compliant body 106.

The compliant body 106 can be formed of any material which allows for bending and flexure as described herein. Inherent material properties combined with size and shape of the compliant body can determine the degree of flexibility. However, non-limiting examples of suitable materials can include polymers (for example, silicone rubber, PDMS, nylon, polyurethane, polyethylene terephthalate), non-magnetizable ductile metals (for example, superelastic Nitinol), and the like. The width of the magnetic robotic device can generally be mesoscale, and as a general guideline can have a width from about 0.1 to about 15 mm, and most often from 1 to 10 mm. The magnetic robotic device can also have any length, and most often 1 mm to 100 mm.

In some examples, a non-magnetic region 107 can be between the first permanent magnet 108a and the second permanent magnet 108b. The non-magnetic region 107 can extend from the first permanent magnet 108a to the second permanent magnet 108b such that there is no magnetic material located between the first permanent magnet 108a and the second permanent magnet 108b. In response to application of a rotating magnetic field generated by the electromagnetic actuator device 102, the magnetic robotic device 104 is operable to be propelled, via undulatory locomotion, through a lumen 110 (e.g., a natural lumen of human). As shown in the 5-sequence scene of FIGS. 1a-1e, as the electromagnetic actuator device 102 rotates (e.g., an omnidirectional electromagnet, or a permanent magnet rotated by a motor), the first and second permanent magnets 108a and 108b are caused to move in different directions, which causes a middle section of the compliant body 106, which can be the non-magnetic region 107, to bend or flex, so that during successive rotations of the electromagnetic actuator device 102, the magnetic robotic device 104 experiences undulatory locomotion (e.g., snake-like movement) through a lumen, in part because of the friction generated between the walls of the lumen 110 and the magnetic robotic device 104. Undulatory locomotion can be considered the type of motion characterized by wave-like movement patterns that act to propel something forward. Examples of this type of gait include crawling in snakes, or swimming in the lamprey.

When the rotation of the magnetic field is reversed, the direction of the robot (e.g., 104) is also reversed. Since this actuation concept is wireless, and because it has no internal moving parts beyond mechanical compliance, this soft-actuator (e.g., 104) is capable of being fabricated at a wide range of scales. In addition, because a permanent magnet can be fabricated as an annulus (e.g., FIG. FIG. 2d), the robot can be fabricated with an internal lumen without interfering with the actuation. Thus, in this case, the permanent magnets are annulus shaped with a center aligned along a longitudinal axis of the compliant body (e.g. a plane of the annulus is perpendicular to the longitudinal axis).

The permanent magnets can be shaped and sized to allow placement and function as described herein. As a general guideline, the permanent magnets can be annulus, cylindrical, cubic, prism, block, or other shapes. An annulus can be particularly useful if maintaining an open bore is a priority, for example to allow passage of fluids or other medical device. A cylinder can be useful if no bore is necessary, in order to maximize strength while having a circular cross section to conform with lumen environments. The permanent magnets can be formed of any suitable permanent magnet materials (i.e. those having a persistent magnetic field otherwise known as magnetically hard materials having a high coercivity greater than approximately 50 kA/m, and most often greater than 500 kA/m). Non-limiting examples of suitable permanent magnetic materials include neodymium based magnets (e.g. NdFeB), aluminum-nickel-cobalt, ferrites (barium ferrite), samarium-cobalt, and the like. Magnets may also be formed in an additive-manufacturing process in which particles of magnetic materials are embedded in a nonmagnetic matrix material. Regardless, such magnetic elements are discretely and specifically oriented as described herein with respect to the compliant body.

Although sizes can vary, the permanent magnets are often from about 0.1 mm to about 15 mm in maximum dimension (i.e. length, width or height), and most often from 1 to 8 mm. These permanent magnets can be spaced apart from one another a distance which allows bending of the non-magnetic region. Again, dimensions can vary somewhat based on size of the device; however, as a general guideline, the non-magnetic region can range from 3 mm to about 30 mm. Furthermore, the number of permanent magnets can vary from two or greater. However, as a general guideline, two to 100, and from two to twenty permanent magnets can be used in some examples.

For the applied rotating non-uniform magnetic field, a magnetic dipole can be implemented. A dipole field has a simple analytic structure that facilitates analysis. Dipole fields are generated by spherical permanent magnets, but the fields of all magnetic sources can be approximated by dipole fields at sufficient distances. Certain permanent magnet geometries can be accurately approximated as dipole fields at even relatively close distances. In one example, spherical permanent magnets and electromagnetic sources whose fields are accurately approximated by dipole fields can be used, as well as methods to generate rotating magnetic fields at arbitrary locations in space and about arbitrary axes using those dipole-field sources. The following discussion also provides a comparison of the use of dipole fields to uniform magnetic fields. However, other non-uniform magnetic fields could be applied that are sufficiently dipole-like (e.g., the field of a cubic or cylindrical permanent magnet).

A rotating non-uniform field (specifically, a rotating dipole field), as opposed to a rotating uniform field (e.g., generated by tri-axial Helmholtz coils) can be used. In a uniform field, all magnetic elements experience the same field as each other at all times, so in a sense, the "non-uniformity" can be introduced in the mechanical design of the device to break the symmetry and cause locomotion in some specific direction. The present technology uses of a non-uniform field that enables the design of a soft robot to be substantially simpler than prior attempts, and as a result enables fabrication at smaller scales. In addition, translating bench-top results that utilize tri-axial Helmholtz coils to a clinical system can be substantially more challenging than translating concepts that utilize non-uniform fields, because it can be easier to place a strong magnetic dipole source near and adjacent to a patient than to fully surround that patient with coils.

In one example, the soft robot actuator and system described herein can be useful in medical applications. The technology can be applied in untethered devices ranging from microrobots, for which there are numerous potential medical applications throughout the human body, to capsule endoscopes for screening, diagnosis, and therapy in the gastrointestinal (GI) tract. In one design, two permanent magnets are embedded in a substantially cylindrical compliant body. As shown in FIG. 2a, a magnetic robotic device 204 can comprise a flexible or compliant tubular body 206 having a central hollow aperture 210 or lumen, a first annular permanent magnet 208a attached to the compliant body 206, and a second annular permanent magnet 208b attached to the compliant body and spatially separated from the first permanent magnet 208a about the compliant body. The central aperture 210 can facilitate flow of bodily fluids, deliver liquid drugs, increase flexibility of the compliant body, or allow passage of medical devices (e.g. endoscopes, snares to remove blood clots, forceps, or the like). In this example, magnetic dipole directions of each permanent magnet are also in a common direction. In some examples, a non-magnetic region 207 can be between the first permanent magnet 208a and the second permanent magnet 208b. The non-magnetic region 207 can extend from the first permanent magnet 208a to the second permanent magnet 208b such that there is no magnetic material located between the first permanent magnet 208a and the second permanent magnet 208b. Each of the magnets includes a north pole (shown as white) and a south pole (shown as black), which can be arranged in an alternating polarity manner as shown (see e.g., FIG. 3a), or in a non-alternating polarity manner (see e.g., FIG. 3b). The compliant body 206 can include a central aperture 210 extending through the compliant body. Note that a number of micro components can be supported by, on or in the compliant body, such as sensors, antennas, chemicals, fluids, etc. Each magnet can be similarly formed having a ring or an annular profile configuration (e.g., a disk with an aperture), and can be embedded in ends or end areas or portions of the compliant body.

In another example, the compliant body can have an exterior shape which increases flexibility. For example, a folded body (i.e. accordion) shape can be useful. Similarly, a cylindrical body can include a series of exterior transverse slits which only partially extend into an exterior surface from opposing sides can allow for increased bending due to slit gaps. Regardless, the compliant body can be made compliant through choice of materials and shape.

Figure 2B:
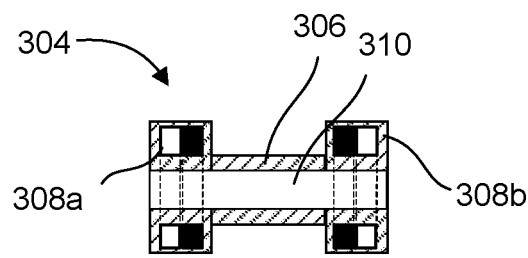
FIG. 2b illustrates a cross sectional view of a magnetic robotic device, in accordance with an example of the present disclosure.

FIG. 2b illustrates another example of a magnetic robotic device 304 that utilizes protrusions from a compliant body 306 to improve propulsion with respect to a lumen. The protrusions can be perimeter sections of the magnets 308a and 308b (e.g., embedded in silicon) that extend radially outwardly from the perimeter circumference of the compliant body 306. Thus, the protruding surfaces of the magnets 308a and 308b can be embedded in a portion of the compliant body (e.g., silicon), or wrapped in another material. Thus, the protrusions, have increased or additional surface area and exposed edges, and can optionally have surface texturing or micropatterning, which can better grasp or grip an inner wall surface of a lumen to increase propulsion speed of the magnetic robotic device 304 (as compared to device 204). The compliant body 306 can also optionally include a central aperture 310 extending through the compliant body.

Figure 2C:
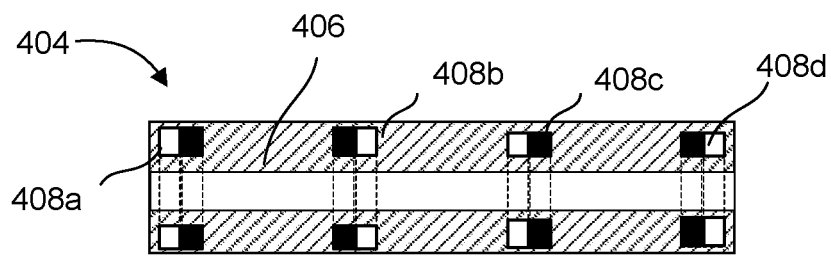
FIG. 2c illustrates a cross sectional view of a magnetic robotic device, in accordance with an example of the present disclosure.

In one example, the system can include embedding more than two permanent magnets and use a soft robot as the distal end of a compliant device such as a catheter to assist in its propulsion. FIG. 2c illustrates a magnetic robotic device 404 comprising a compliant body 406 and a four permanent magnets 408a-d separated and distributed along a length of the compliant body 406. Typically, the permanent magnets can be longitudinally spaced along the length of the compliant body such that there are only a single permanent magnet along each longitudinal position. As shown, magnets 408a and 408b have a common magnetic direction, magnets 408b and 408c are alternating in polarity and magnetic direction, and magnets 408c and 408d also have a common magnetic direction. In some examples, a non-magnetic region can exist between each pair of adjacent permanent magnets 408a-d. For example, adjacent permanent magnet pairs 408a and 408b, 408b and 408c, and 408c and 408d may each be separated by a non-magnetic region. The nonmagnetic regions can be of sufficient length to allow a bending moment in between the two neighboring permanent magnets.

Figure 2D:
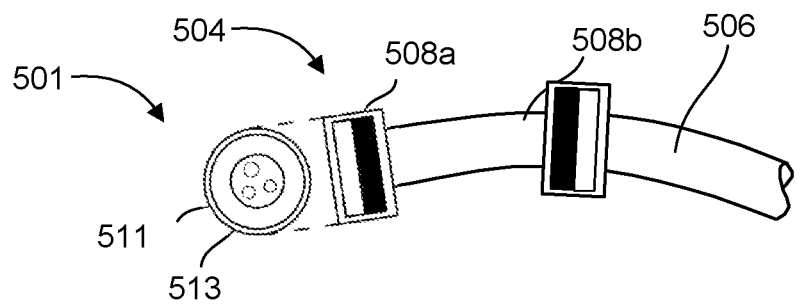
FIG. 2d illustrates a cross sectional view of a magnetic robotic device as part of a catheter device, and showing a front view of the catheter device, in accordance with an example of the present disclosure.

In one example shown in FIG. 2d, a magnetic robotic device 504 can be placed, attached, embedded, or otherwise coupled to the distal end of a continuum device 501, such as a catheter or endoscope, while still allowing fluid flow. More specifically, a first permanent magnet 508a can be attached to one end of a compliant body 506 (e.g., end or tube of a catheter or endoscope), and a second permanent magnet 508b can be attached to another portion of the compliant body 506. As shown in the front view image, a lumen support body 511 of the compliant body 506 can be disposed through central apertures of the magnets 508a and 508b. The lumen support body 511 can comprise at least one lumen 513 for allowing support of a device (e.g., light, camera) or a fluid, gas, or other medium or device. This can enable the tip of the device 501 to assist in propulsion by moving itself forward as the device is pushed from the proximal end, such as by a catheter or endoscope housing or body or other medical device component. Furthermore, the compliant body 506 may have multiple lumens formed therein. For example, the compliant body of FIG. 2d has three internal lumens.

The present disclosure further compares rotating dipole and uniform applied magnetic fields, and alternating and non-alternating embedded-magnet polarities, such as shown and labeled in FIGS. 3a-d, and such combination can result in very effective propulsion of a magnetic robotic device (e.g., a "soft robot", as also termed herein).

In one example, two permanent magnets with alternating polarity can be embedded in a soft robot and rotating non-uniform (dipole-like) field that sweeps over the robot to induce a traveling wave (such as a field generated by operation of an omnidirectional electromagnet, as further described in PCT Patent App. No. PCT/US13/65678 filed Oct. 13, 2013, and as also described in U.S. patent Ser. No. 14/223,510 filed Mar. 24, 2014 each of which are incorporated herein by reference). Each of the permanent magnets has a magnetic dipole m that points along the axis of the magnets. When a magnetic dipole m is placed in a magnetic field b, a torque τ is induced, which attempts to align the dipole with the applied field:

$$\tau = m \times b \tag{1}$$

and a force f is induced due to the spatial derivative in the applied field, which attempts to translate the dipole to a location with a stronger field:

$$f = (m \cdot \nabla) b \tag{2}$$

The dipole field generated by some actuator dipole $m_a$ at each point p in space:

$$b(p) = \frac{\mu_0}{4\pi \|p\|^5} (3 p p^T - I \|p\|^2) m_a \tag{3}$$

decays as $\sim p^{-3}$ (as does the torque that it generates on some other dipole), and the spatial derivatives decay as $\sim p^{-4}$ (as does the force that it generates on some other dipole). As a result, when projecting magnetic fields over distances, the effects of magnetic torque tend to dominate those of magnetic force. In a uniform field (e.g., generated by tri-axial Helmholtz coils), there are negligible differences spatially in the field, and as a result there are negligible forces on the embedded magnets.

Figure 3A:
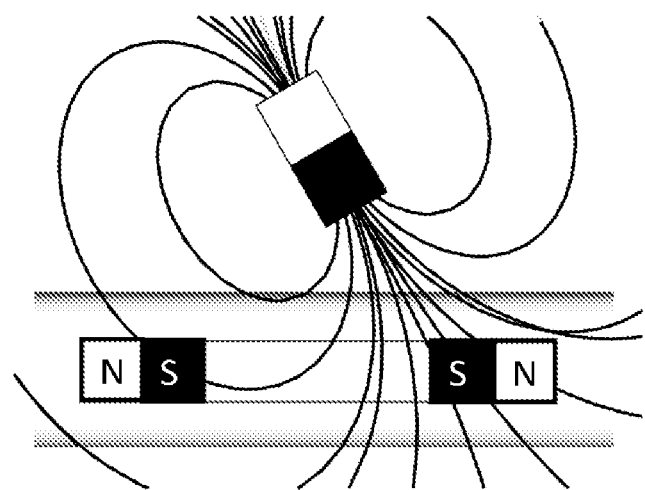
FIGS. 3a-d illustrate four different examples of a system for propelling a magnetic robotic device, in accordance with an example of the present disclosure.
Figure 3B:
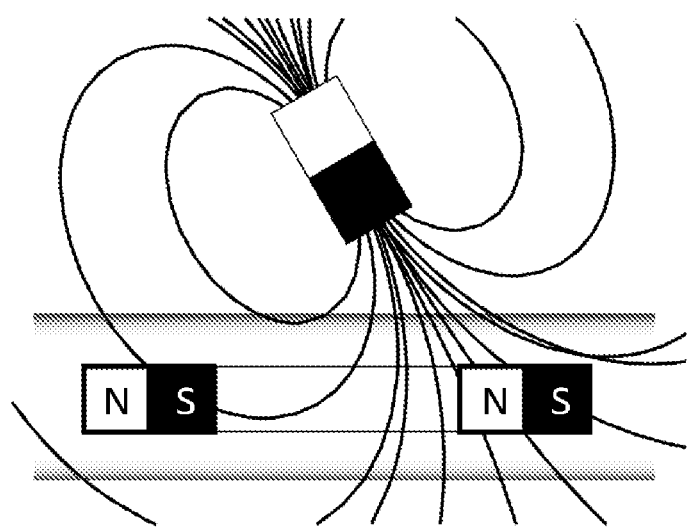
Figure 3C:
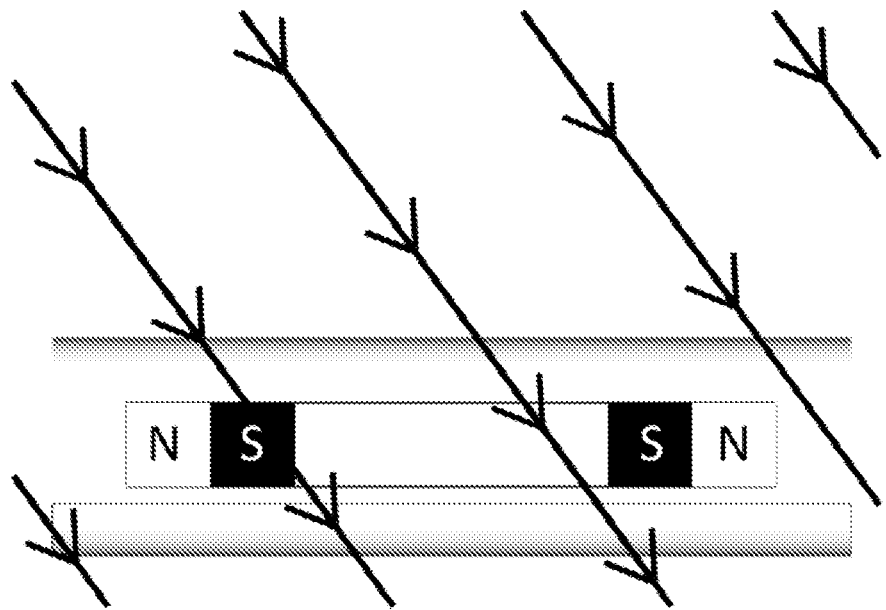
Figure 3D:
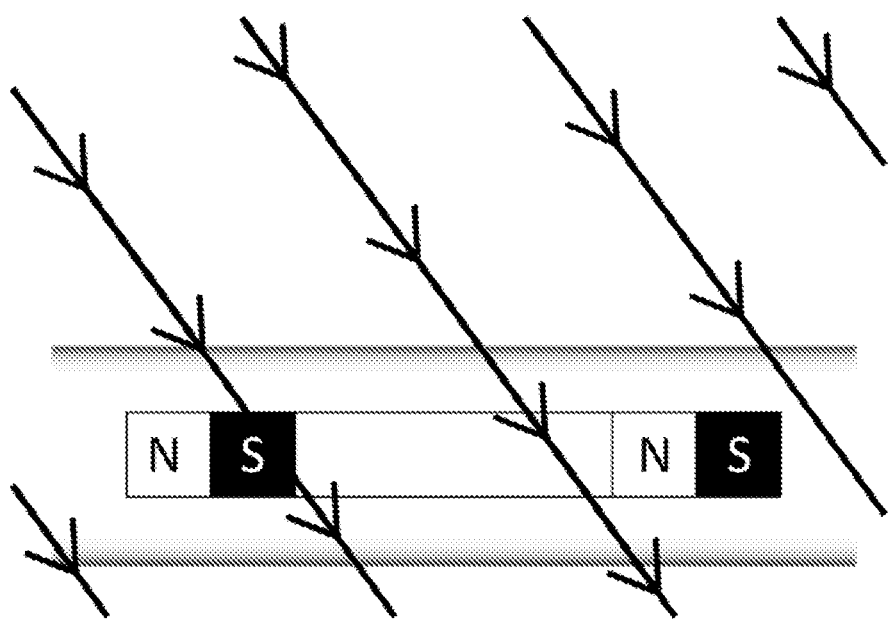

A simple way to think about the hypothesized beneficial effect of using a rotating non-uniform (dipole) field is that the magnets embedded in the soft robot experience approximately the same field as each other, but out of phase (e.g., one magnet experiences a component of the rotating field before the other, as depicted in FIG. 3a), because the magnets are located at distinct, albeit close, points in the field. The result is that a rotating field will cause a traveling wave in a certain deterministic direction; if the field rotation is reversed, then the direction of the traveling wave will also reverse. As the wave travels across the robot's body, any portion of the robot in contact with the lumen will move less than portions not in contact (due to friction with the lumen's walls), resulting in an undulatory locomotion in a deterministic direction. In contrast, in a uniform field we expect the field to bend the robot, but with nothing to cause a net translation in some specific direction (at least not due to torque-based bending).

The polarization of the permanent magnets embedded in the soft robot is also important. In the case of alternating magnets, the magnetic torques applied to the two magnets will tend to be opposite one another, which may excite the first bending mode (i.e., result in a single large-amplitude arc, as depicted in frames 1, 3, and 5 of FIG. 1a, FIG. 1c and FIG. 1e, respectively). With non-alternating magnets, the magnetic torques applied to the two magnets will tend to be approximately the same as one another, which may excite the second bending mode (i.e., result in a sinusoidal shape with two small-amplitude arcs). Note that larger deflections may cause larger contractions per half cycle (particularly as the field strength decreases), and may enable greater distances to be traversed in a single cycle.

The soft robot actuator and rotating-magnet actuation system, including a soft robot and an omnidirectional electromagnet, of the examples discussed herein can be particularly useful in a wide variety of applications. For example, the omnidirectional electromagnet can be configured for use in propelling or controlling or manipulating an object as described hereinabove, such as an in vivo medical device (e.g. a capsule endoscope, magnetically tipped catheter, MEMS for eye surgery or exploration, cochlear implant, urinary or reproductive surgical device, dexterous manipulator, endoscopic camera, swimming and crawling microscale and mesoscale device, magnetic screw, etc.). In one aspect, an object or device (e.g., soft robot) controlled or manipulated by a rotating magnet can include a magnetic component for the application of one or both of a force and torque. In a particular example, a rotating magnet can be used to maneuver a magnetically controlled capsule endoscope, such as in a gastrointestinal tract of a patient. In this case, the capsule or soft robot can be swallowed and observed in the esophagus, stomach, intestines, and/or colon utilizing a camera. The maneuverability of the robot can be used to enhance diagnostic endoscopy as well as enable therapeutic capsule endoscopy. Additional non-limiting examples of applications can include manipulation of a device within the vasculature (i.e., blood vessels), in the cochlea of the inner ear, in the urinary tract, and a device within a pipe or pipe-like structure.

The omnidirectional electromagnet can also be configured as a modular system that is readily attachable and replaceable from existing equipment. Multiple omnidirectional electromagnets can be configured for a specific medical procedure based on the anatomy of the patient and the procedure to be conducted, and the same omnidirectional electromagnets can be reconfigured for a new patient and procedure with minimal effort. The optimal number of omnidirectional electromagnets for a given procedure should not be assumed to be the same as the optimal number for a different procedure. Additionally, the size and strength of the individual omnidirectional electromagnets should not be assumed to be the same within a given procedure.

Example 1

Figure 4A:
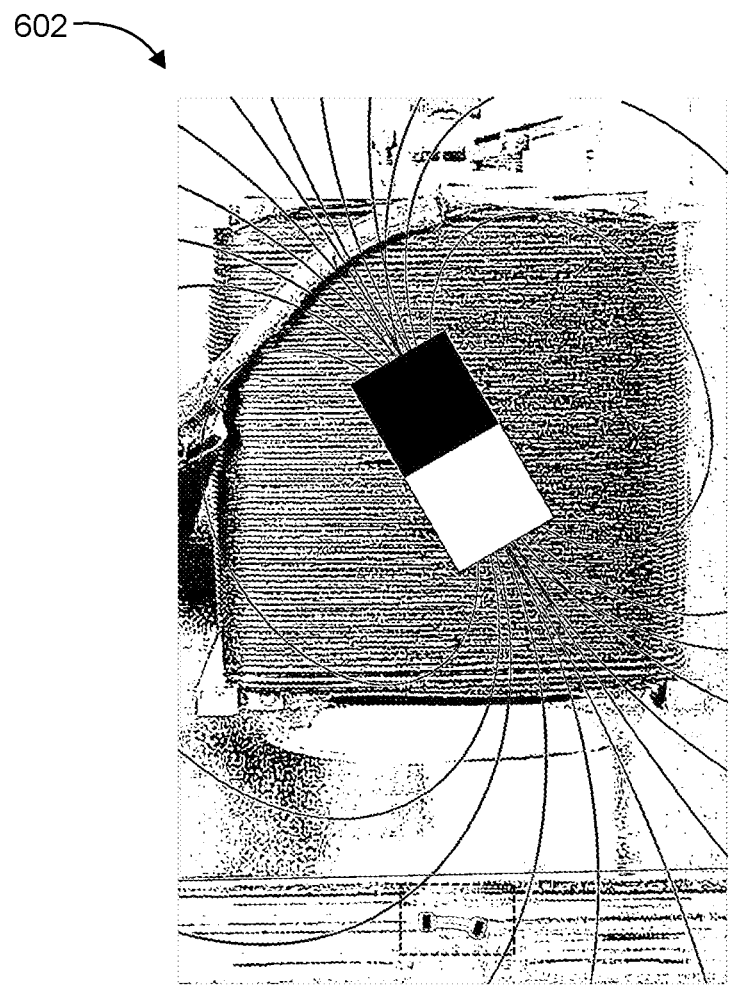
FIGS. 4a-c illustrate an experimental set up system for propelling a magnetic robotic device, in accordance with an example of the present disclosure.

As shown in FIG. 4a, an electromagnetic actuator device 602 is shown in one example as an Omnimagnet electromagnet, which is a device with a cubic form-factor comprising three densely packed, mutually orthogonal electromagnetic coils surrounding a spherical ferromagnetic core, such as described in Patent App. No. PCT/US13/65678 filed Oct. 13, 2013, and as also described in U.S. application Ser. No. 14/223,510 filed Mar. 24, 2014 which are each incorporated herein by reference. However, other systems which form a manipulable magnetic field can also be used. For example, rotating permanent magnet systems can also be used such as, but not limited to, U.S. Pat. No. 8,803,643 which is incorporated herein by reference. The Omnimagnet is capable of generating dipole-like fields by controlling the three currents sourced to its coils. The dipole moment of an Omnimagnet is composed of two parts—the dipole moment of the electromagnetic coils, and the dipole moment of the ferromagnetic core that is magnetized by the coils, and both parts are approximately linear with respect to the applied currents (for the magnitude of currents considered here). In one very specific example, an Omnimagnet was optimized to be accurately modeled by the point-dipole model, and that model may be quite accurate at distances (from its center) greater than a 1.5 minimum-bounding-sphere radii. The Omnimagnet that may be used for this purpose can be the type described in A. J. Petruska, J. B. Brink, and J. J. Abbott, "First demonstration of a modular and reconfigurable magnetic-manipulation system," in Proc. *IEEE Int. Conf. Robotics and Automation*, 2015, pp. 149-155 which is also incorporated herein by reference. This model has a cubic dimension of 127 mm, a minimum-bounding-sphere radius of 90 mm, and a maximum dipole strength of 50 A·m$^2$ at 8 A applied current. Each coil is driven by an Advanced Motion Control 30A8 PWM servo drive, capable of 15 A continuous current, all powered by an Advanced Motion Control PS16L72 power supply with maximum DC output voltage of 72 V. Since each coil can be modeled as a RL circuit, the maximum frequency without attenuation, based on the amplifiers, power supply, coil resistance and inductance, is 97 Hz at 8 A.

Figure 4B:
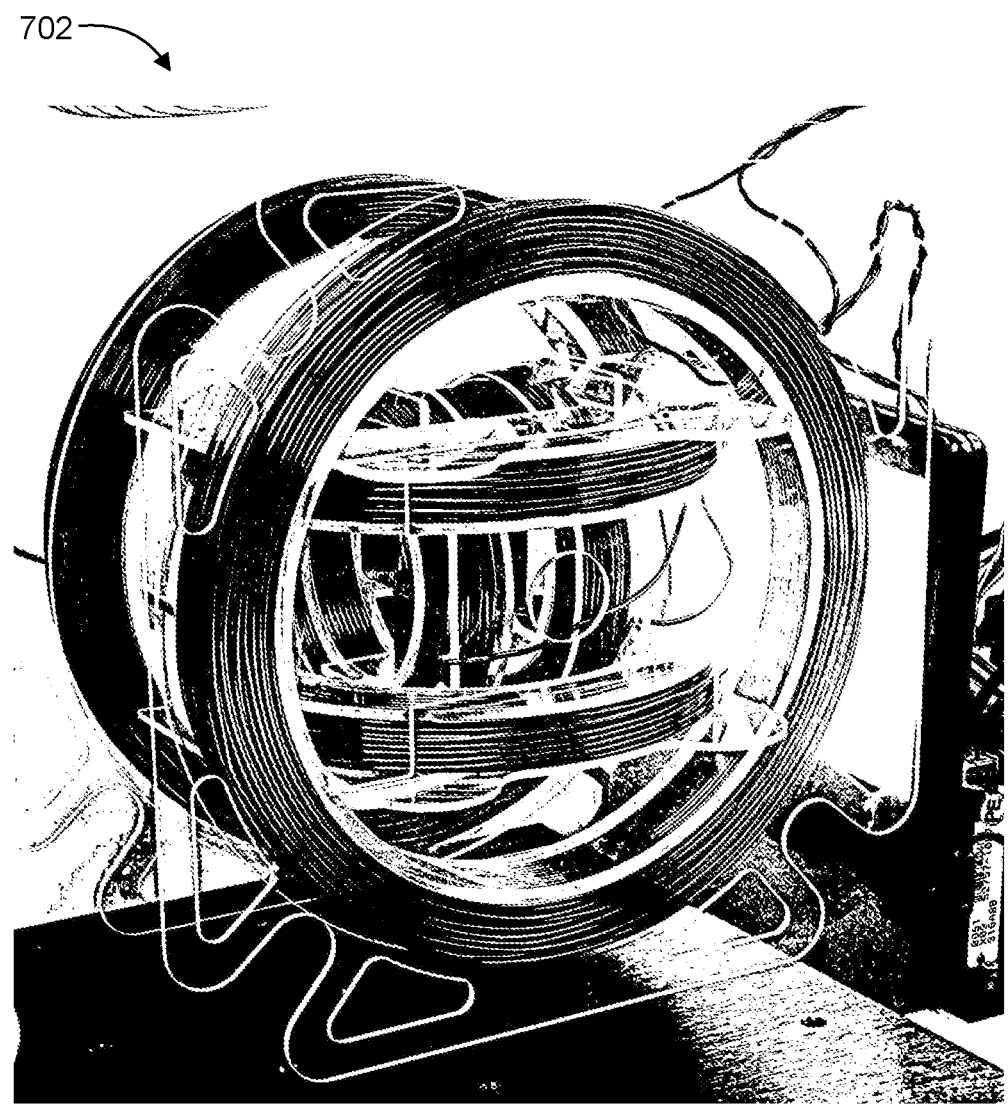

As shown in FIG. 4b, an electromagnetic actuator device 702 is shown in one example as tri-axial Helmholtz Coils, which is a system of three orthogonally nested sets of Helmholtz coils (note that each "Helmholtz coil" is actually two co-axial coils connected in series). Each Helmholtz coil generates a magnetic field that is optimally uniform at the center of the workspace, is aligned with the axis of the coil, and varies linearly with the electric current flowing through the coil. Three orthogonal coils enables the magnetic field vector to be assigned arbitrarily, with each Helmholtz coil corresponding to a basis direction in the field. Details of this system's construction is provided in A. W. Mahoney, J. C. Sarrazin, E. Bamberg, and J. J. Abbott, "Velocity control with gravity compensation for magnetic helical microswimmers," *Advanced Robotics*, vol. 25, pp. 1007-1028, 2011 which is incorporated herein by reference. Each Helmholtz coil is driven by an Advanced Motion Controls S16A8 PWM analog servo drive, capable of 8 A continuous current with 24 V supplied by an Advanced Motion Control PS2X300W power supply. Since each Helmholtz coil can be modeled as a RL circuit, the maximum frequency without attenuation, based on the amplifiers, power supply, coil resistance and inductance, is 208 Hz at 8 A.

Figure 4C:
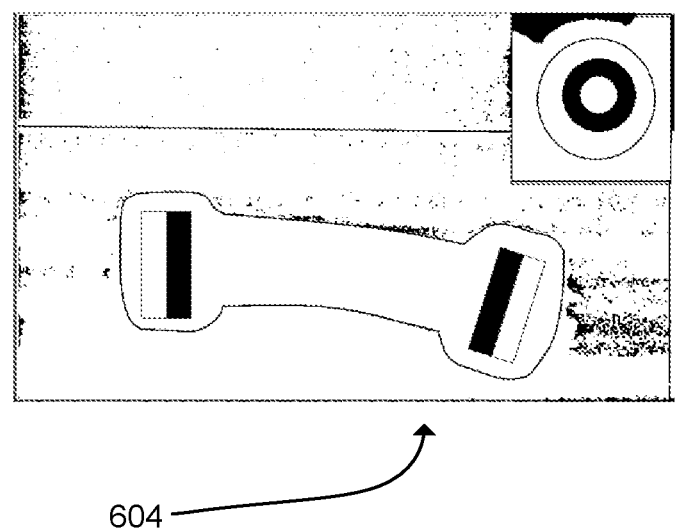
Figure 5A:
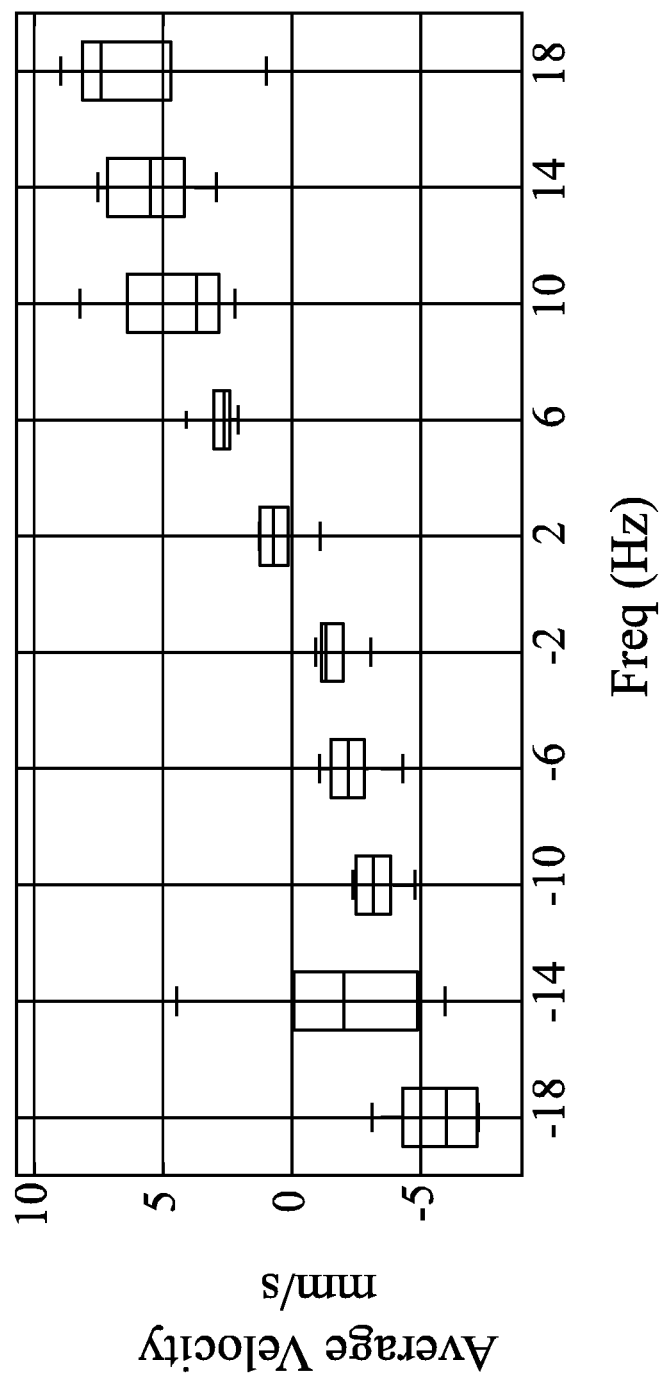
FIGS. 5a-d are box-and-whisker plots of average velocity of four different systems for propelling a magnetic robotic device, in accordance with an example of the present disclosure.
Figure 5B:
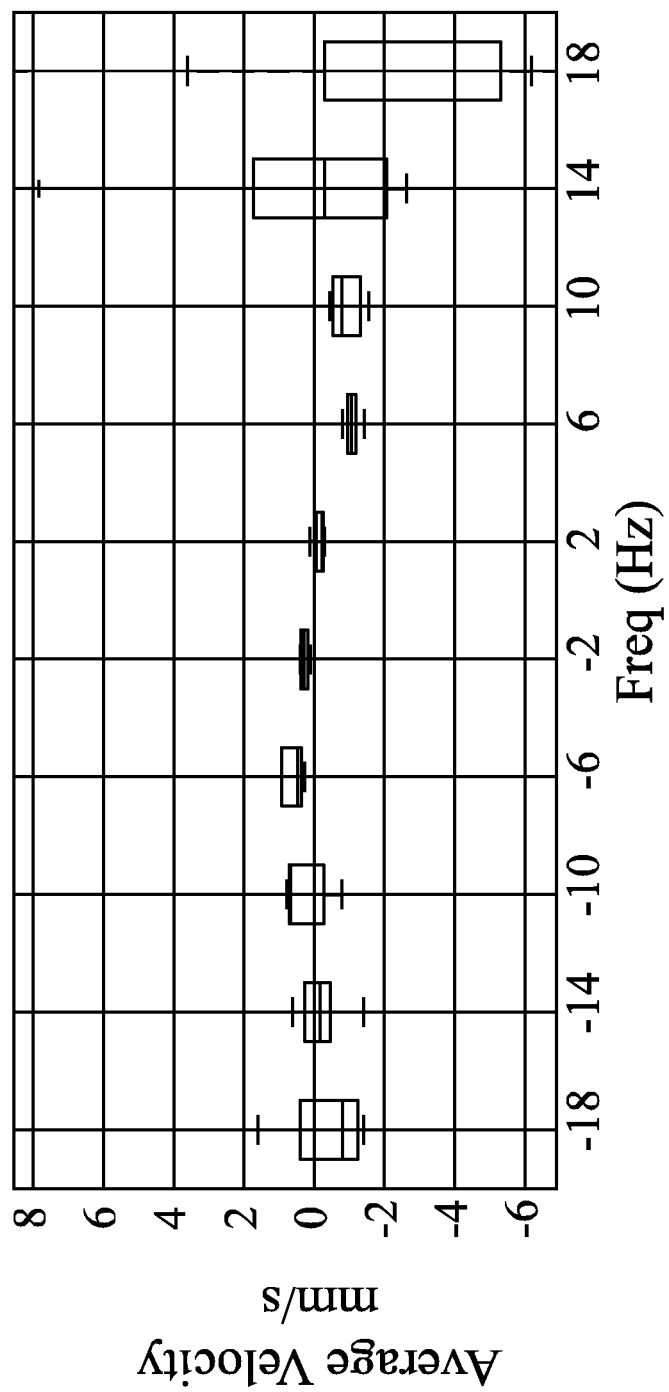
Figure 5C:
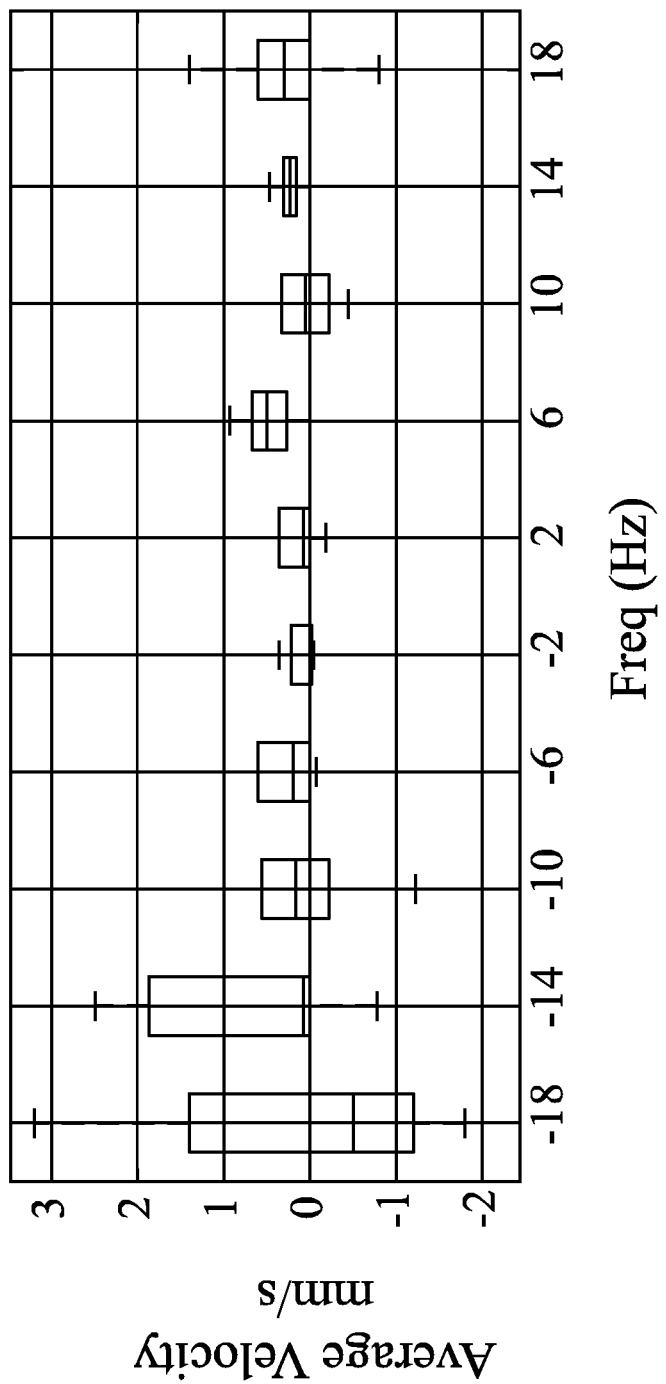
Figure 5D:
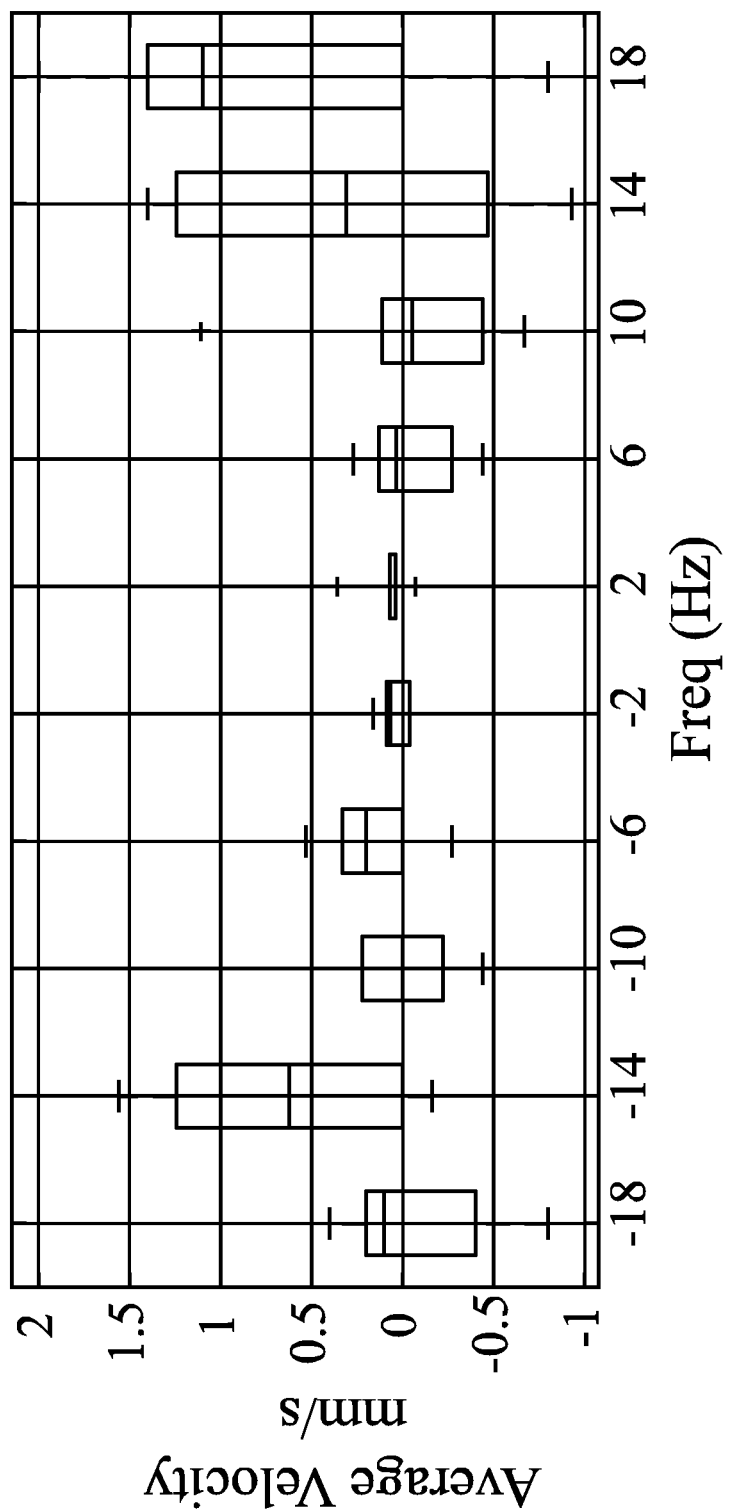
Figure 6A:
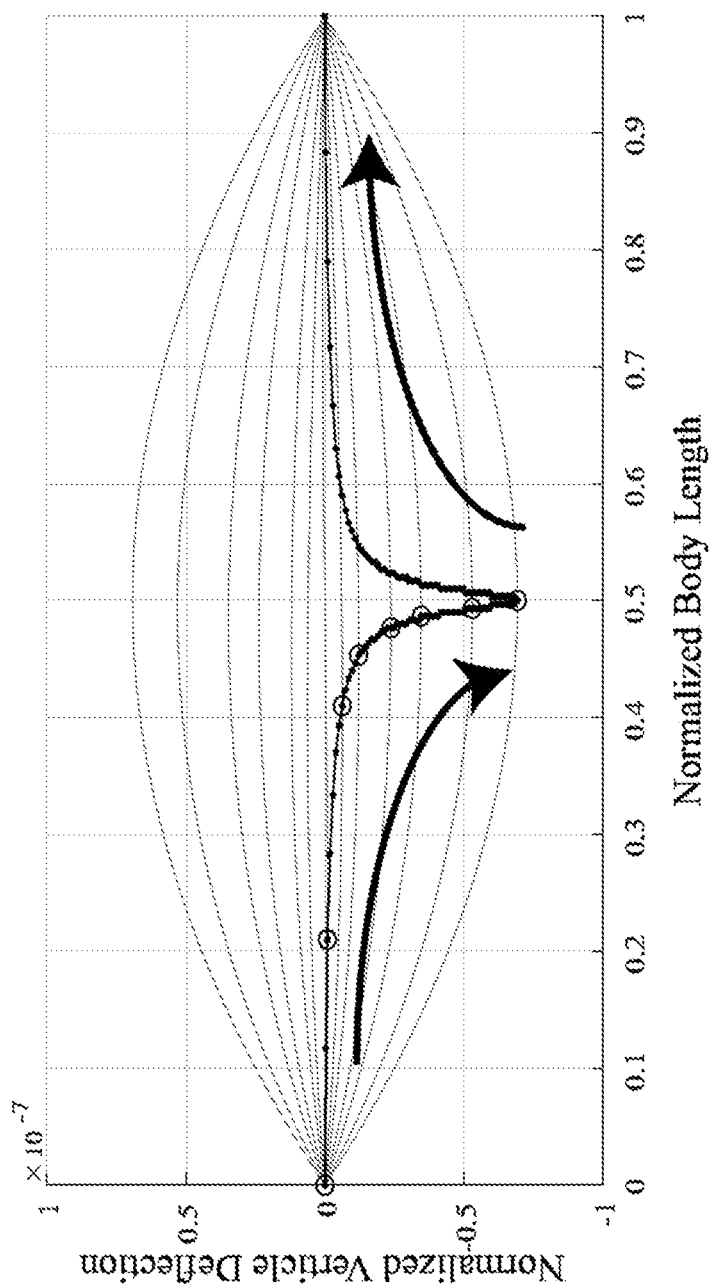
FIGS. 6a-d are graphs of four different systems for propelling a magnetic robotic device for one rotation of a magnetic field in each system, in accordance with an example of the present disclosure.
Figure 6B:
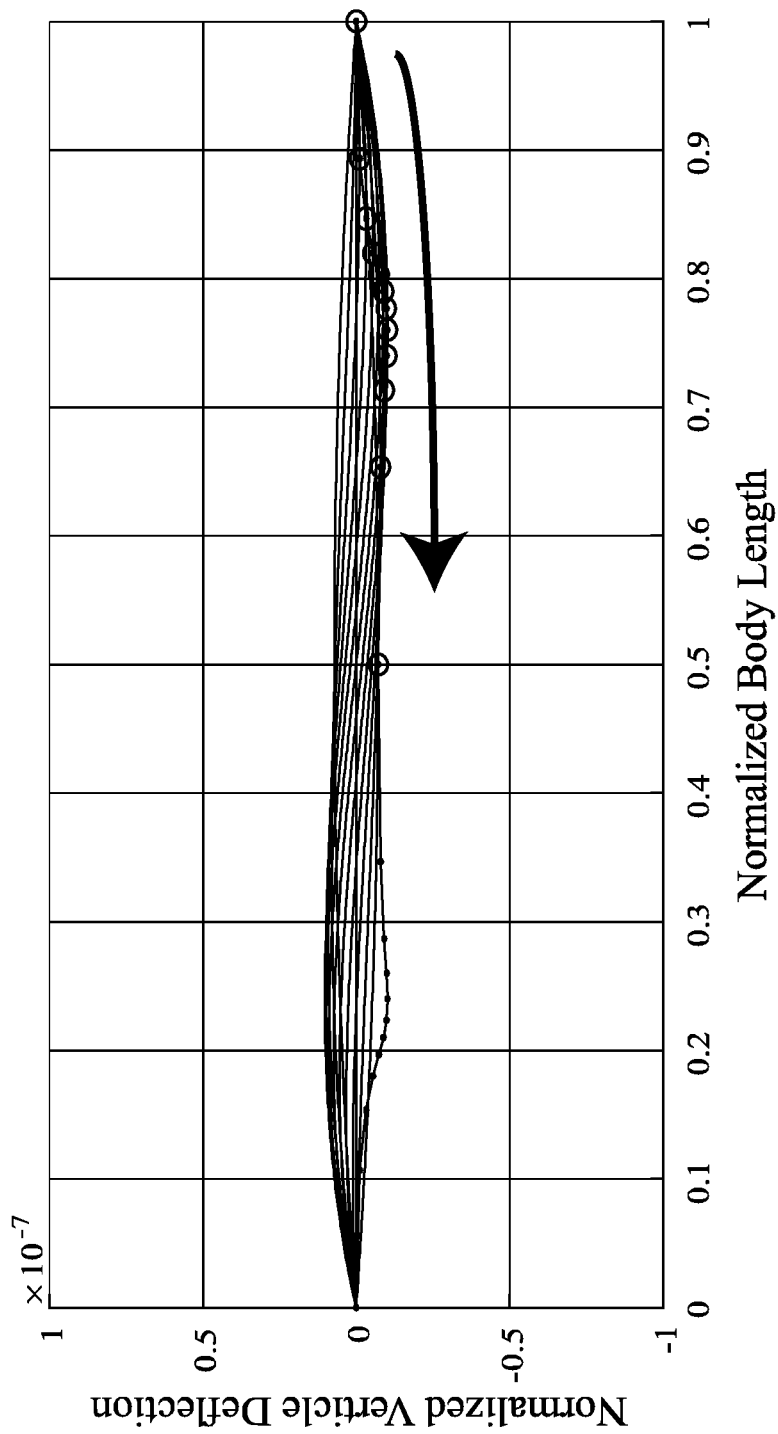
Figure 6C:
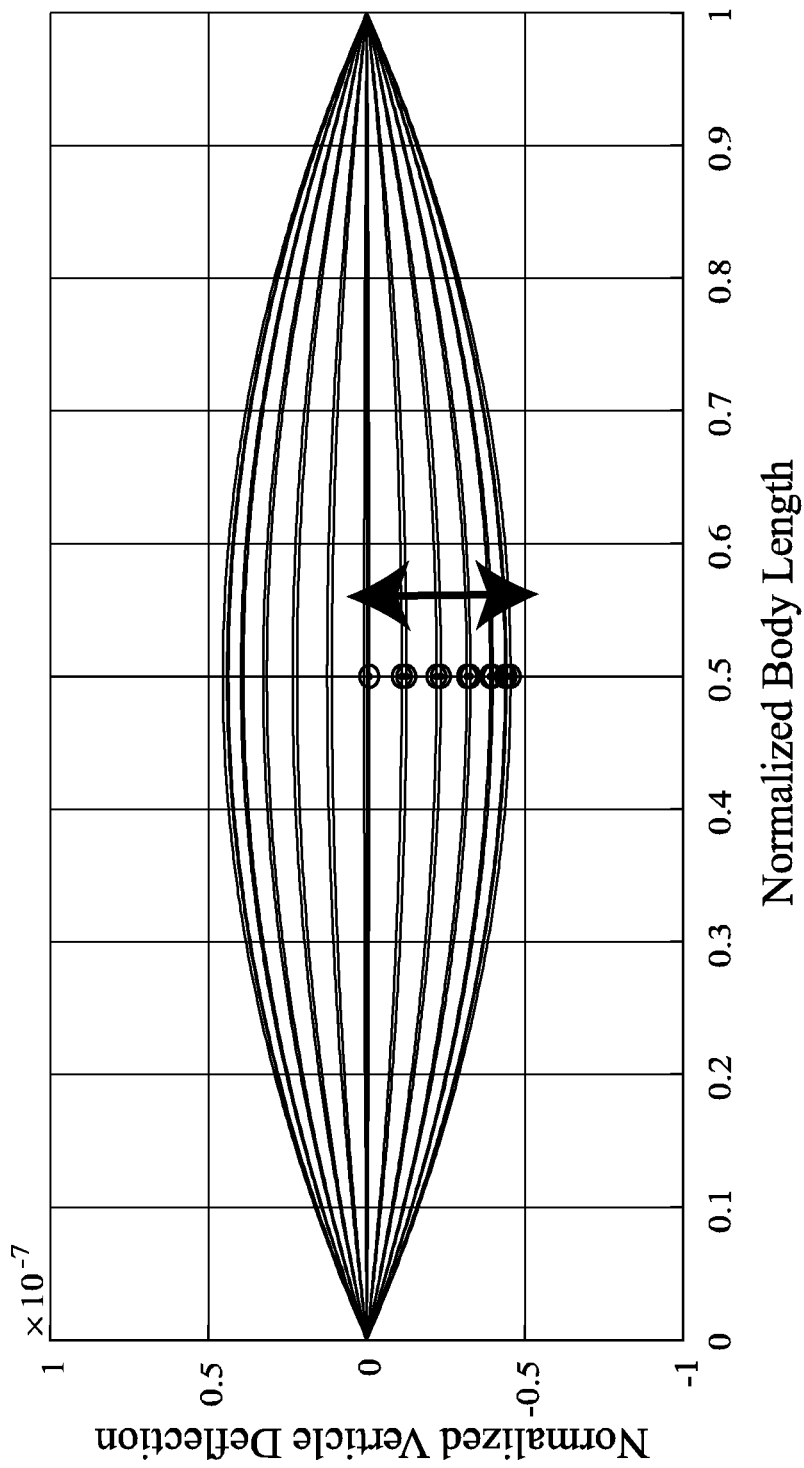
Figure 6D:
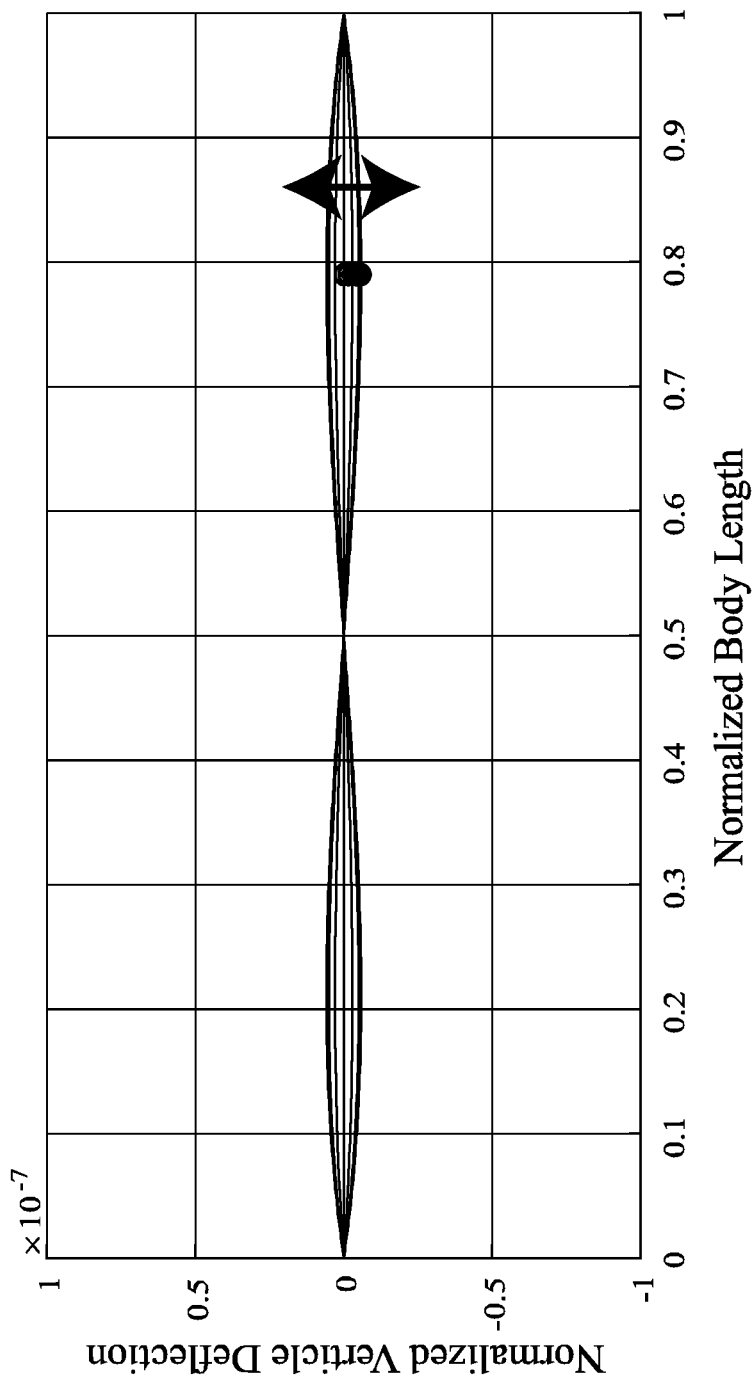

As shown in the example of FIG. 4c, various examples of "soft robots" or magnetic robotic devices, such as magnetic robotic device 604, can be fabricated using a compliant or flexible or semi-flexible material, such as Dragon Skin 20 silicone, injected into a mold with two annular magnets threaded through a wire. The wire, once removed, creates a 1-mm-diameter lumen through the robot. The robot is 5 mm in diameter over the magnets, 2.5 mm in diameter at the central region, and 20 mm in total length. In one example, the soft robot includes an alternating polarity, and another soft robot can have non-alternating polarity. The permanent magnets were Grade-N42 NdFeB magnets, axially magnetized, with 3 mm outer diameter, 1.5 mm inner diameter, 1.5 mm thickness, and with dipole strength of 0.0107 A·m$^2$.

In one experiment and example, a soft robot was placed into a transparent tube with a 6 mm inner diameter, and it was recorded for either the time it took for the robot to travel 20 mm or the distance traveled in 90 cycles, whichever occurred first. The value of 20 mm was chosen in order to stay within the small-angle approximation below the Omnimagnet, such that the distance from the center of the Omnimagnet to the soft robot was approximately constant. Trials were performed at frequency intervals between ~18 Hz to 18 Hz (10 frequencies). Experiments were performed in sets of 20 random combinations of frequency and magnet polarity. Six to eight sets of data were recorded for each frequency in FIGS. 5a-d.

For dipole (Omnimagnet) experiments and as an example, as shown in FIG. 4a the tube was placed in the horizontal plane below the Omnimagnet, 135 mm directly below its center (sufficiently far such that the point-dipole model is quite accurate). A dipole strength of 40 A·m$^2$ was rotated around an axis in the horizontal plane that is orthogonal to the axis of the tube and robot. This resulted in peak field strength of 1.72 mT at the robot, with the field strength varying by a magnitude of approximately two throughout the rotation cycle. Depending on the direction of travel (from pilot studies), the robot would be placed 10 mm either to the left or right of the tube's center. Rotating the dipole field would then cause the robot to travel directly under the Omnimagnet, where the field is the strongest, and after 20 mm of travel the robot would be 10 mm on the opposite side of the tube.

Uniform-field (tri-axial Helmholtz coils) experiments were performed at 1.72 mT field strength, which was the peak field value directly below the Omnimagnet in the rotating-dipole experiments described above. The tube was placed into the uniform workspace of the Helmholtz coils, with the robot placed directly at the center of the tube, since there was no expected direction of travel.

The results of one experimental study are shown in FIGS. 5*a-d*. From these experiments, three main conclusions and associated benefits and advantages are provided. First, the alternating-polarity robot in a dipole field shows a strong correlation between the frequency of rotation and the robot velocity. The relationship appears approximately linear and consistent for low frequencies (−10 Hz to 10 Hz), but becomes more erratic at higher frequencies. Second, the non-alternating-polarity robot in a dipole field shows a small linear relationship between the frequency of field rotation and the robot velocity for low frequencies (−6 Hz to 6 Hz). The resulting velocity is slower and in the opposite direction of the alternating-polarity robot. At higher frequencies the average velocity is negligible, and the velocity in any given trial is erratic. Third, in uniform fields, regardless of the polarization of the magnets, there is no clear correlation between the field rotation frequency and the resulting robot velocity, with data straddling 0 mm/s at all frequencies.

The movement of the robot can be complex and involve magnetic forces, vibrations, surface inconsistencies, and contact between the tube and robot. However, the experimental results discussed above highlight two major factors that contribute to the robot propulsion: the non-uniformity of the rotating magnetic field, and the alternating polarity of the robot magnets. A simple numerical simulation is provided that describes how the robot can deflect and how it correlates with the experimental results. The structure is modeled as an elastic beam with roller constraints on the ends. These constrains allow the magnets to freely rotate and translate horizontally, but constrains them from translating vertically to approximate the constraint imposed by a lumen. The four cases that can be considered are the same as those in the experiments, depicted in FIG. 3, and they include the four combinations of field type (dipole or uniform) and magnet polarity (alternating or non-alternating).

For a given pair of magnetic torques applied at the ends of the beam, the deflection of the beam is calculated using the following differential equation $$EI\frac{d^2}{dx^2}v(x) = M(x) \quad (4)$$

where x is a point along the beam, v(x) is the vertical displacement at each point, M(x) the bending moment at each point, E the modulus of elasticity, and I the second moment of area of the beam's cross-section. The local slope of the beam is calculated as dv(x)/dx. The solution for v(x) is provided below.

For a given magnetic field (dipole or uniform), the torque on each of the embedded magnets is calculated using equation (1), and then solved for the beam deflection using equation (4). The slope at the beam ends dictate the new orientation of the embedded magnets, and these orientations are used to update the torque and re-solve for the beam deflection. This process is repeated until the beam deflection converges on an equilibrium solution. After each update of the magnetic field by a small rotation, the previous beam solution is used to seed the search for the new beam solution. In one example, a dipole field source can be located 135 mm above the beam, with a dipole strength of $m_a$=40 A·m². A beam with a length of 20 mm can be used, as well as magnets with dipole strength of m=0.0107 A·m². These choices were used for consistency with the experimental setup (see FIG. 4*c*). Simulation results over one rotation of the magnetic field are shown by the grey lines in FIGS. 6*a-d*, with the circles and arrows highlighting the motion for half a cycle. The results suggest that the use of non-uniform magnetic fields is useful, and for both cases there is a clear traveling wave, whereas uniform fields will cause the beam to deflect in a standing wave. The results also suggest that alternating the polarities of the embedded magnets results in substantially larger deflections than with non-alternating polarity. This is because alternating the polarity results in excitation of the first bending mode of the beam, whereas non-alternating polarity excites the stiffer second bending mode.

This numerical study supports that the alternating-magnet robot may travel faster than the non-alternating-magnet robot due to larger body deformations, and deterministic directionality can be created by a traveling wave induced by the dipole field, whereas the uniform field is expected to cause no net movement; and the non-alternating-magnet robot is expected to travel in the opposite direction from the alternating-magnet robot.

The present disclosure describes an actuation concept to enable a mesoscale soft robot to locomote through lumens. The technology can comprise a soft robot with two or more embedded permanent magnets with alternating magnetic polarity, and a rotating non-uniform (dipole) magnetic field that is swept over the robot, resulting in a traveling-wave undulatory motion that propels the robot forward and backward. Experiments and numerical simulations confirm the benefits of using non-uniform dipole fields over using uniform fields, as well as the benefits of alternating the polarity of the magnets embedded in the device.

Example 2

Figure 7:
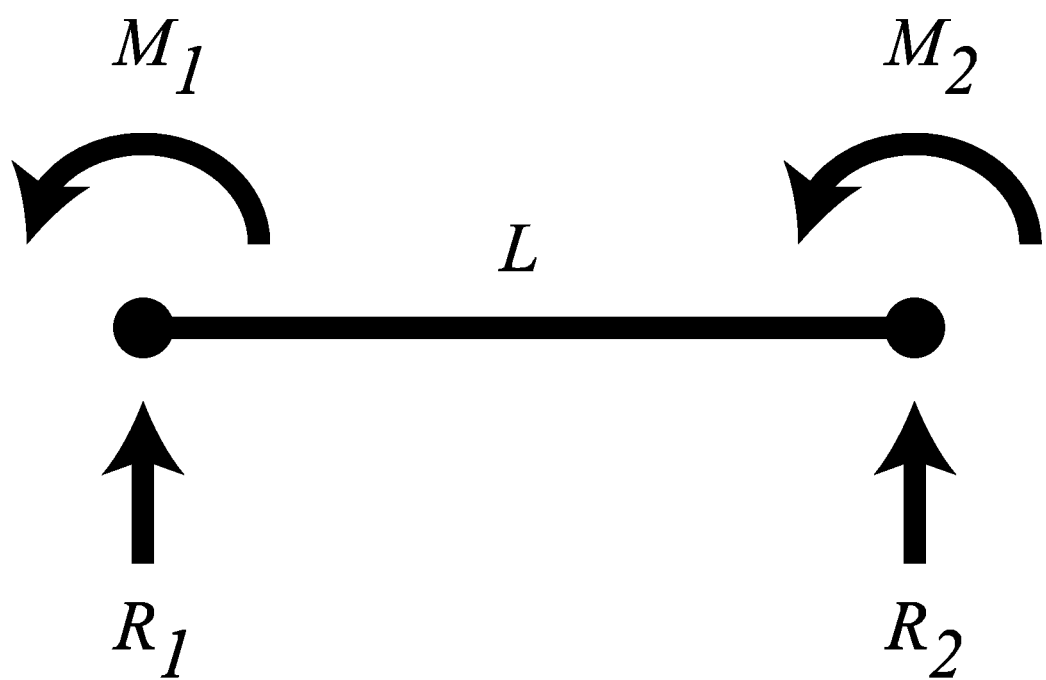
FIG. 7 is a free body diagram of a beam with roller supports, as pertaining to a magnetic robotic device, in accordance with an example of the present disclosure.

This example details a solution for a particular case where the deflection v(x) and slope dv(x)=dx of an elastic beam, based on equation (4), are used above. The flexural rigidity of the beam (EI) is presumed to be constant along the beam, and small deflections. The bending moment M acting on the beam at a distance x from the left end can be derived from the free body diagram in FIG. 7:

$$M(x) = -M_1 + R_1 x \quad (5)$$

Substituting (5) into (4) and integrating yields the slope of the beam, dv(x)/dx:

$$EI\frac{d^2}{dx^2}v(x) = -M_1 x + \frac{R_1}{2}x^2 + C_1 \quad (6)$$

Integrating again gives the deflection of the beam, v(x):

$$EIv(x) = \frac{-M_1}{2}x^2 + \frac{R_1}{6}x^3 + C_1 x + C_2 \quad (7)$$

In total, there are four unknowns: $R_1$, $R_2$, $C_1$, and $C_2$. The boundary conditions provide two constraint equations:

$$v(0) = 0 \Rightarrow 0 = C_2 \qquad (8)$$

$$v(L) = 0 \Rightarrow 0 = \frac{-M_1}{2}L^2 + \frac{R_1}{6}L^3 + C_1 L \qquad (9)$$

Static equilibrium provides the other two constraints:

$$\Sigma F = 0 \Rightarrow R_1 + R_2 = 0 \qquad (10)$$

$$\Sigma M = 0 \Rightarrow M_1 - R_1 L + M_2 = 0 \qquad (11)$$

Solving (9)-(11) gives:

$$R_1 = \frac{M_1 + M_2}{L} \qquad (12)$$

$$R_2 = \frac{-(M_1 + M_2)}{L} \qquad (13)$$

$$C_1 = \frac{LM_1}{3} - \frac{LM_2}{6} \qquad (14)$$

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

What is claimed is:

1. A magnetic robotic device, comprising:
a compliant body;
a first permanent magnet attached to the compliant body;
a second permanent magnet attached to the compliant body and spatially separated from the first permanent magnet about the compliant body; and
a non-magnetic region between the first permanent magnet and the second permanent magnet,
wherein, in response to application of a rotating magnetic field generated by a magnetic actuator device, the magnetic robotic device is operable to be propelled, via undulatory locomotion of the magnetic robotic device.

2. The magnetic robotic device of claim 1, wherein the first and second permanent magnets comprise alternating magnetic polarity from one another.

3. The magnetic robotic device of claim 1, wherein the first and second permanent magnets comprise non-alternating magnetic polarity from one another.

4. The magnetic robotic device of claim 1, wherein the magnetic robotic device is untethered to a structure, such that the magnetic robotic device is configured to freely travel or move through a human without constraint from an inorganic element.

5. The magnetic robotic device of claim 1, wherein the first and second permanent magnets are attached at an opposite ends of the compliant body.

6. The magnetic device of claim 5, wherein the non-magnetic region extends from the first permanent magnet to the second permanent magnet.

7. The magnetic robotic device of claim 1, further comprising a third permanent magnet attached to the compliant body and spatially separated from the second permanent magnet by a non-magnetic region.

8. The magnetic robotic device of claim 1, wherein the compliant body comprises a tubular body having at least one lumen disposed therein and wherein each of the first and second permanent magnets comprise an annular magnet profile configuration extending around the at least one lumen.

9. The magnetic robotic device of claim 1, wherein the first permanent magnet and the second permanent magnet are attached to an external surface of the compliant body.

10. The magnetic robotic device of claim 1, wherein the first permanent magnet and the second permanent magnet are embedded in the compliant body.

11. The magnetic robotic device of claim 1, wherein the magnetic robotic device is sized and shaped to fit within at least some natural lumens of a human.

12. A method of propelling the magnetic robotic device of claim 1 through a human, the method comprising operating the magnetic actuator device proximate the magnetic robotic device to generate a non-uniform magnetic dipole field, thereby effectuating undulatory motion of the magnetic robotic device for locomotion through the human.

13. A system for propelling a magnetic robotic device through a human, comprising:
a magnetic actuator device operable to generate a rotating magnetic field; and
a magnetic robotic device comprising a compliant body and at least two permanent magnets supported by the compliant body, such that the at least two permanent magnets are spatially separated from each other by nonmagnetic regions along a length of the compliant body,
wherein, in response to application of the rotating magnetic field by the magnetic actuator device situated proximate the magnetic robotic device, the rotating magnetic field effectuates undulatory locomotion of the magnetic robotic device to propel the magnetic robotic device.

14. The system of claim 13, wherein the magnetic actuator device comprises an electromagnetic actuator with two or more electromagnetic coils.

15. The system of claim 14, wherein the electromagnetic actuator device comprises an omnidirectional electromagnet.

16. The system of claim 13, wherein the magnetic actuator device comprises a permanent magnet.

17. The system of claim 13, wherein the magnetic actuator device is operable to rotate a non-uniform magnetic dipole field about the magnetic robotic device.

18. The system of claim 13, wherein the magnetic actuator device is operable to reverse the direction of the rotating magnetic field to propel the magnetic robotic device in a generally opposite direction.

19. The system of claim 13, wherein the at least two permanent magnets include a first pair of permanent magnets and the system further comprising a catheter having a distal end that includes the compliant body, wherein the first pair of permanent magnets is attached to the distal end for assisting with propulsion of the distal end of the catheter through the human.

20. The system of claim 19, wherein each of the first pair of permanent magnets comprise an annular profile defining a central aperture, where the compliant body comprises a lumen support body that extends through the central apertures of the first pair of permanent magnets, the lumen support body comprising at least one lumen extending through the lumen support body.

* * * * *